(12) United States Patent
Weeber et al.

(10) Patent No.: US 8,894,204 B2
(45) Date of Patent: Nov. 25, 2014

(54) OPHTHALMIC LENS, SYSTEMS AND METHODS HAVING AT LEAST ONE ROTATIONALLY ASYMMETRIC DIFFRACTIVE STRUCTURE

(75) Inventors: Hendrik A. Weeber, Groningen (NL); Scott J. Catlin, Orange, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 397 days.

(21) Appl. No.: 13/328,292

(22) Filed: Dec. 16, 2011

(65) Prior Publication Data

US 2012/0320335 A1 Dec. 20, 2012

Related U.S. Application Data

(63) Continuation-in-part of application No. 12/971,506, filed on Dec. 17, 2010, now Pat. No. 8,430,508, and a continuation-in-part of application No. 12/971,607, filed on Dec. 17, 2010, now Pat. No. 8,480,228, and a continuation-in-part of application No. 12/971,889, filed on Dec. 17, 2010, now Pat. No. 8,444,267.

(60) Provisional application No. 61/424,433, filed on Dec. 17, 2010.

(51) Int. Cl.
G02C 7/02 (2006.01)
G02C 7/04 (2006.01)
A61F 2/16 (2006.01)

(52) U.S. Cl.
CPC ....... *A61F 2/1618* (2013.01); *A61F 2002/1645* (2013.01); *A61F 2/1654* (2013.01); *G02C 2202/20* (2013.01); *G02C 7/041* (2013.01)
USPC ............. 351/159.52; 351/159.35; 351/159.44

(58) Field of Classification Search
USPC ............. 351/159.01, 159.02, 159.11–159.13, 351/159.15, 159.26, 159.35, 159.44, 351/159.74–159.77, 159.52
See application file for complete search history.

(56) References Cited

U.S. PATENT DOCUMENTS

| | | |
|---|---|---|
| 3,367,734 A | 2/1968 | Bystricky et al. |
| 4,637,697 A | 1/1987 | Freeman |
| 4,642,112 A | 2/1987 | Freeman |
| 4,655,565 A | 4/1987 | Freeman |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,932,970 A | 6/1990 | Portney |
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,144,483 A | 9/1992 | Cohen |
| 5,225,858 A | 7/1993 | Portney |
| 5,229,797 A | 7/1993 | Futhey et al. |
| 5,652,638 A | 7/1997 | Roffman et al. |
| 5,699,142 A | 12/1997 | Lee et al. |
| 5,748,282 A | 5/1998 | Freeman |
| 5,760,871 A | 6/1998 | Kosoburd et al. |
| 5,796,462 A | 8/1998 | Roffman et al. |
| 5,968,094 A | 10/1999 | Werblin et al. |
| 6,126,283 A | 10/2000 | Wen et al. |
| 6,126,286 A | 10/2000 | Portney |
| 6,142,625 A | 11/2000 | Sawano et al. |
| 6,210,005 B1 | 4/2001 | Portney |
| 6,338,559 B1 | 1/2002 | Williams et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |

(Continued)

FOREIGN PATENT DOCUMENTS

| | | |
|---|---|---|
| EP | 0343067 A1 | 11/1989 |
| EP | 457553 A2 | 11/1991 |

(Continued)

OTHER PUBLICATIONS

International Search Report and Written Opinion for Application No. PCT/US2011/065433, mailed on Mar. 23, 2012, 4 pages.
Alfonso J.F., et al., "Prospective Study of the Acri.LISA bifocal Intraocular Lens," Journal of Cataract Refractive Surgery, 2007, vol. 33 (11), pp. 1930-1935.
Canovas C., et al., "Hybrid Adaptive-Optics Visual Simulator," Optical Letters, 2010, vol. 35 (2), pp. 196-198.
Cohen, Allen L., "Practical design of a bifocal hologram contact lens or intraocular lens," Applied Optics, 1992, 31 (19), 3750-3754.
Co-pending U.S. Appl. No. 12/771, 550, filed Apr 30, 2010.
Diffractive Lenses for Extended Depth of Focus and Presbyopic Correction. Presentation from Wavefront Congress held on Feb. 15, 2008, Rochester, New York.

(Continued)

*Primary Examiner* — Darryl J Collins
(74) *Attorney, Agent, or Firm* — Abbott Medical Optics Inc.

(57) ABSTRACT

An ophthalmic lens, such as an intraocular lens (IOL), a phakic IOL or a corneal implant, and a system and method relating to same, having coupled thereto and/or integrated thereon at least one rotationally asymmetric diffractive structure. The lens of the present invention may include a single or limited number of rotationally asymmetric diffractive echelettes that provides an extended depth of focus.

12 Claims, 9 Drawing Sheets

(56) References Cited

U.S. PATENT DOCUMENTS

| | | |
|---|---|---|
| 6,609,793 B2 | 8/2003 | Norrby et al. |
| 6,705,729 B2 | 3/2004 | Piers et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,475,986 B2 | 1/2009 | Dai et al. |
| 7,615,073 B2 | 11/2009 | Deacon et al. |
| 7,871,162 B2 | 1/2011 | Weeber |
| 2002/0118337 A1 | 8/2002 | Perrott et al. |
| 2003/0076478 A1 | 4/2003 | Cox |
| 2003/0171808 A1 | 9/2003 | Phillips |
| 2004/0021824 A1 | 2/2004 | Ye et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0230299 A1 | 11/2004 | Simpson et al. |
| 2005/0096226 A1 | 5/2005 | Stock et al. |
| 2005/0128432 A1 | 6/2005 | Altmann |
| 2005/0203619 A1 | 9/2005 | Altmann |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0176572 A1 | 8/2006 | Fiala |
| 2006/0238702 A1 | 10/2006 | Glick et al. |
| 2006/0244904 A1 | 11/2006 | Hong et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0295295 A1 | 12/2009 | Shannon et al. |
| 2009/0323020 A1 | 12/2009 | Zhao et al. |
| 2010/0161048 A1 | 6/2010 | Schaper, Jr. |

FOREIGN PATENT DOCUMENTS

| | | |
|---|---|---|
| EP | 681198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | WO2007092948 A1 | 8/2007 |
| WO | WO2007133384 A2 | 11/2007 |
| WO | WO2008045847 A2 | 4/2008 |
| WO | WO2009076670 A1 | 6/2009 |

OTHER PUBLICATIONS

Doskolovich L.L., et al., "Special Diffractive Lenses," SPIE, 1992, vol. 1780, pp. 393-402.

International Search Report and Written Opinion for Application No. PCT/IB2011/001067, mailed on Sep. 13, 2011, 13 pages.

International Search Report for Application No. PCT/EP2008/061235, mailed on Mar. 5, 2009, 2 pages.

International Search Report for Application No. PCT/EP2009/051783, mailed on Apr. 28, 2009, 3 pages.

International Search Report for Application No. PCT/IB2009/005590, mailed on Sep. 30, 2009, 3 pages.

International Search Report for Application No. PCT/US08/073999, mailed on Dec. 3, 2008, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

International Search Report for Application No. PCT/US2010/061017, mailed on Jun. 16, 2011, 7 pages.

International Search Report for Application No. PCT/US2010/061042, mailed on Mar. 31, 2011, 3 pages.

International Search Report for Application No. PCT/US2010/061081, mailed on Jun. 6, 2011, 7 pages.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived From Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.

Norrby S., et al., "Model Eyes for Evaluation of Intraocular Lenses," Applied Optics, 2007, vol. 46 (26), pp. 6595-6605.

Partial International Search Report for Application No. PCT/US2010/061081, mailed on Apr. 6, 2011, 2 pages.

Piers P.A., et al., "Eye Models for the Prediction of Contrast Vision in Patients with New Intraocular Lens Designs," Optics Letters, 2004, vol. 29 (7), pp. 733-735.

Piers P.A., et al., "Theoretical Comparison of Aberration-Correcting Customized and Aspheric Intraocular Lenses," Journal of Refractive Surgery, 2007, vol. 23 (4), pp. 374-384.

Siedlecki D., et al., "Radial Gradient index Intraocular Lens: a Theoretical Model," Journal of Modern Optics, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

(56) References Cited

OTHER PUBLICATIONS

Van Meeteren A., "Calculations on the Optical Modulation Transfer Function of the Human Eye for White Light," Optica Acta, 1974, vol. 21 (5), pp. 395-412.

Vanden Berg T.J., "Analysis of Intraocular Straylight, Especially in Relation to Age," Optometry and Vision Science, 1995, vol. 72 (2), pp. 52-59.

Villegas E.A., et al., "Correlation between Optical and Psychophy, Sical Parameters as a Function of Defocus," Optometry and Vision Science, 2002, vol. 79 (1), pp. 60-67.

OPHTHALMIC LENS, SYSTEMS AND METHODS HAVING AT LEAST ONE ROTATIONALLY ASYMMETRIC DIFFRACTIVE STRUCTURE

CROSS-REFERENCES TO RELATED APPLICATIONS

This application claims priority to U.S. provisional application No. 61/424,433 filed on Dec. 17, 2010, the entire contents of which are incorporated herein by reference. This application is also a Continuation-In-Part application of the following U.S. patent applications: Single Microstructure Lens, Systems And Methods, U.S. patent application Ser. No.: 12/971,506; Limited Echelette Lens, Systems And Methods, U.S. patent application Ser. No. 12/971,607; and Ophthalmic Lens, Systems And Methods With Angular Varying Phase Delay, U.S. patent application Ser. No.: 12/971,889. The entire contents of these three applications are also incorporated herein by reference. This application is also related to the following U.S. Patent Application Ser. Nos.: 61/047,699 and 12/109,251, both filed on Apr. 24, 2008; Ser. No. 12/429,155 filed on Apr. 23, 2009; Ser. No. 12/372,573 filed on Feb. 17, 2009; Ser. No. 12/197,249 filed on Aug. 23, 2008; Ser. No.12/120,201 filed on Apr. 13, 2008, and Ser. No. 12/771,550 filed on Apr. 30, 2010.

BACKGROUND OF THE INVENTION

1. Field of the Invention

This invention relates generally to a system, method and apparatus for providing an ophthalmic lens, and more particularly, to a lens, system and method having at least one rotationally asymmetric diffractive structure.

2. Description of the Related Art

Surgery on the human eye has become commonplace in recent years. Many patients pursue eye surgery as an elective procedure, such as to avoid the use of contacts or glasses. Other patients pursue surgery to correct an adverse condition in the eye. Such adverse conditions may include, for example, cataracts or presbyopia, as well as other conditions known to those skilled in the art that may adversely affect elements of the eye.

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, also referred to as the lens capsule, or capsular bag. Image formation in the eye occurs by entry of image-forming light to the eye through the cornea, and refraction by the cornea and the crystalline lens to focus the image-forming light on the retina. The retina provides the light sensitive tissue of the eye.

Ophthalmic lenses, such as intraocular lenses (IOLs), phakic IOLs and corneal implants may be used to enhance or correct vision, such as to correct for the aforementioned adverse conditions, including aberrations or inadequacies that adversely affect the performance of the referenced structures of the eye. For example, IOLs are routinely used to replace the crystalline lens of an eye that is removed during cataract surgery.

By way of example, an ophthalmic lens in the form of an IOL may be spheric/aspheric or toric. Spheric/aspheric IOLs may be used for correction of a myriad of vision problems, while toric IOLs are typically used specifically for astigmatic eye correction. Generally, astigmatism is an optical defect in which vision is blurred due to the ocular inability to focus a point object into a sharply focused image on the retina. This may be due to an irregular, or toric, curvature of the cornea and/or eye lens. When using an IOL, the angular orientation of the IOL in the eye is of particular importance since a toric IOL is intended to be inserted at a specific angle. If the insertion angle is not correct and/or maintained, any preoperative astigmatism will not be fully corrected, and in fact the astigmatic condition may worsen. The condition caused by this misalignment of the IOL is often referred to as residual cylinder, or remaining astigmatism.

More particularly, toric IOLs are generally to be positioned in the eye such that the cylinder axis of the IOL is properly aligned with the cylinder axis of the patient's cornea. Thus, ophthalmic lenses, such as IOLs, are typically sensitive to cylinder orientation misalignment relative to that to be corrected, such as wherein the axis of the toric lens in the eye and the lens for correction are not accurately aligned. Further, typical toric lenses are highly sensitive to a mismatch between the intended postoperative refraction and the power of the selected lens. Suboptimal lens designs may arise due to these sensitivities based on measurement errors, unintended changes of cylinder power and/or axis during or after surgery, or because lenses are offered only in a number of discrete cylinder increments and/or powers.

Thus, a need exists for a lens apparatus, system and method that improve the performance of toric ophthalmic lenses.

SUMMARY OF THE INVENTION

The present invention is and includes at least an ophthalmic lens, such as an intraocular lens (IOL), a phakic IOL or a corneal implant, and a system and method relating to same, having coupled thereto at least one rotationally asymmetric diffractive structure. The lens of the present invention may include one or more surface regions having a refractive optical power and/or a diffractive optical power that together enhance vision.

More particularly, embodiments of the present invention may include an optic having at least a toric portion for correcting astigmatism and having a base cylinder power, and a rotationally asymmetric, single or limited number of diffractive echelettes for extending depth of focus. The rotational asymmetry may be with respect to the shape of the single or limited diffractive echelette(s) with respect to the optical axis. In other words, rather than have a concentric echelette(s) in the shape of a circle, the echelette(s) may be in the shape of an ellipse, or any other shape that is rotationally asymmetric with respect to the optical axis. The rotational asymmetry may also be the result of a variable stepheight along the echelette(s). In standard diffractive IOLs the echelette stepheight remains constant, although the stepheight between echelettes may vary. Here, in a single echelette embodiment for example, the stepheight may vary tangentially as a function of the rotational angle. The extended depth of focus accomplished by the rotational asymmetry disclosed herein may reduce sensitivity of the optic to at least one of rotation and the base cylinder power. Additionally, the rotational asymmetry may result in a differential depth of focus along predetermined meridians.

Systems and methods in accordance with the present invention may include any manner of providing an ophthalmic lens having one or more rotationally asymmetric structures. Such systems and method may include, and/or may be executed by, for example, hardware, software, and computing systems and processes.

Thus, the present invention provides a lens, system and method that improve the performance of lenses, and particularly of multifocal and/or toric ophthalmic lenses.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and in which.

Figure 1:
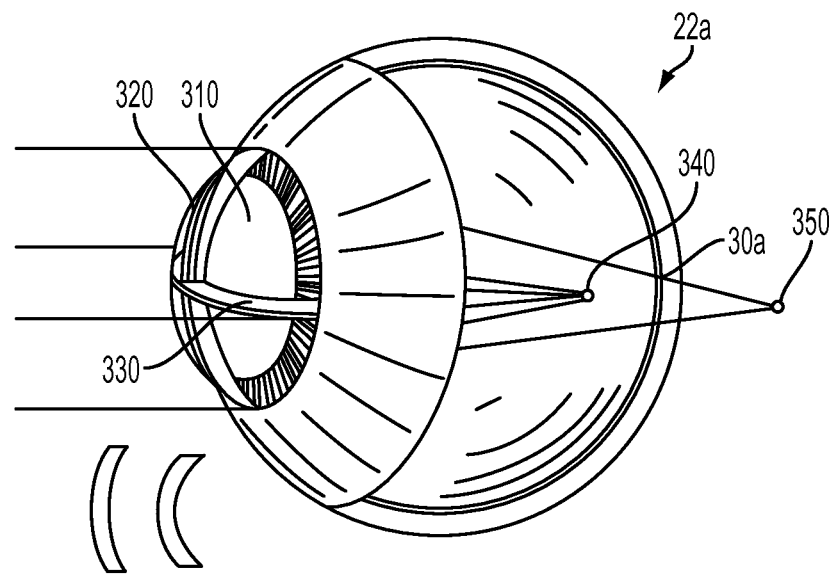
FIG. 1 is a schematic illustration of an eye.

For illustration purposes, the profile geometries shown in certain aforementioned figures were not drawn exactly to scale. The heights of the profiles shown in the figures are generally on the order of about 0.5 µm to about 8.0 µm although the heights may vary depending on factors such as the amount of correction needed by the patient, the refractive index of the lens material and surrounding medium, and the desired phase shift/delay.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical lenses, lens systems and methods. Those of ordinary skill in the pertinent arts may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the pertinent arts.

The present invention is directed to an ophthalmic lens, such as, for example, contact lenses, corneal inlays or onlays, or intraocular lenses (IOLs) including, for example, phakic IOLs and piggyback IOLs) and a system and method relating to same, having thereupon at least one rotationally asymmetric diffractive structure. The lens of the present invention may include one or more surface regions having a refractive optical power and/or a diffractive optical power that together enhance vision. The terms "power" or "optical power" are used herein to indicate the ability of a lens, an optic, an optical surface, or at least a portion of an optical surface, to redirect incident light for the purpose of forming a real or virtual focal point. Optical power may result from reflection, refraction, diffraction, or some combination thereof and is generally expressed in units of Diopters. One of skill in the art will appreciate that the optical power of a surface, lens, or optic is generally equal to the reciprocal of the focal length of the surface, lens, or optic, when the focal length is expressed in units of meters. Further, as used herein, the term "refractive optical power" or "refractive power" includes optical power produced by the refraction of light as it interacts with a surface, lens, or optic, and the term "diffractive optical power" or "diffractive power" includes optical power resulting from the diffraction of light as it interacts with a surface, lens, or optic.

More particularly, in embodiments of the present invention, an ophthalmic lens may include one or a limited number of rotationally asymmetric diffractive echelettes that provide an extended depth of focus, thereby producing a corrective lens having decreased sensitivity to alignment errors and to selection of the proper cylinder power in corrective optics. The embodiments of the corrective lens, system and method of the present invention thus provide an improved performance after implantation, such as by at least decreasing dependence of any residual astigmatism on surgical skill and postoperative patient healing. The present invention is directed to ophthalmic lenses, such as IOLs, phakic IOLs, contact lenses, spectacle lenses, and corneal inlays, as well as corneal reshaping procedures and combinations of the foregoing.

FIG. 1 depicts an eye 22a with a corneal astigmatism. Eye 22a of FIG. 1 includes a cornea 310 having a first curvature 320 on a first meridian, and a second curvature 330 on a second meridian that is perpendicular to the first meridian. Although FIG. 1 depicts one meridian vertically and another meridian horizontally, the set of two perpendicular meridians may have any orientation, that is, may be rotated around the optical axis. The variation in curvature along the meridians causes two foci to be imaged by the eye. The distance between the foci represents the astigmatism.

More specifically, a first focus 340 may be created by first curvature 320 in cornea 310, and a second focus 350 may be created by second curvature 330 in cornea 310. Since the first focus 340 and the second focus 350 are not on the retina 30a, as shown, the foci cannot be on the retina 30a simultaneously using only spherical correction. Consequently, blurry vision results.

A corrective lens may be used to correct for the astigmatism generated within the cornea 310 correspondent to the unique foci of first curvature 320 and second curvature 330. Such a corrective lens may be a toric lens that has a curvature difference between two perpendicular meridians matched to that of the cornea (first curvature 320 and second curvature 330), but having an oppositely signed (+/−) astigmatism.

Figure 2:
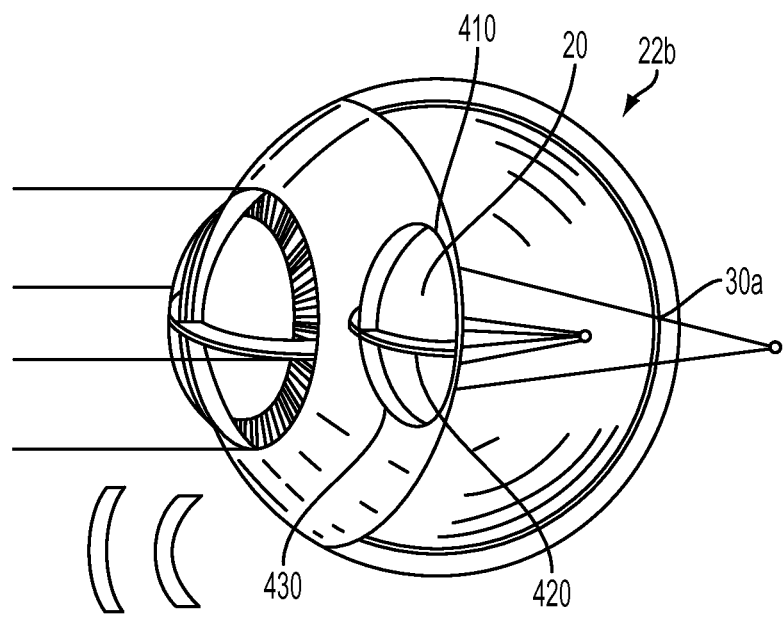
FIG. 2 is a schematic illustration of an eye.

FIG. 2 illustrates an eye 22b having corrected astigmatism. Eye 22b is similar to the astigmatic eye 22a discussed above with the addition of IOL 20. IOL 20 may be toric in design, having a first curvature 420 and a second curvature 430. In order to substantially correct the astigmatism of eye 22b, it is necessary that curvature 420 matches curvature 320, and that curvature 430 matches curvature 330, although partial correction may also be achieved by having a substantial curvature match in each axis. In addition to matching the curvatures, the correction lens should be aligned with the cornea in order to achieve optimal correction. Misalignments in the angle of the IOL, either by surgical placement or by post surgical movement, may leave some residual astigmatism as discussed above.

IOL may comprise of one or more fixation members or haptics which secure the IOL in the eye. The haptics may be made of the same material as optic and/or integrally formed therewith. Alternatively, one or more haptics may be formed separately and attached to optic. The haptics may comprise any of a variety of materials which exhibit sufficient supporting strength and resilience, and/or which are substantially biologically inert in an intended in-vivo environment. Suitable materials for this purpose include, for example, polymeric materials such as silicone polymeric materials, acrylic polymeric materials, hydrogel-forming polymeric materials, such as polyhydroxyethylmethacrylate, polyphosphazenes, polyurethanes, and mixtures thereof and the like. In other exemplary embodiments, ophthalmic lens may include a positioning means that allows optic to move along optical axis in response to deformation of the capsular bag and/or in response to the ciliary muscles of the eye.

As used herein, the terms "extended focus", "depth of focus" or "extended depth of focus" (collectively "EDOF") include a depth of focus of a test lens, optic, or optical element that exceeds the depth of focus of a reference optic. The EDOF may be attributable to a particular feature, structure, or mask, such as the rotationally asymmetric diffractive element discussed further herein.

According to an aspect of the present invention, a corrective lens, such as IOL 20, may include a diffractive element designed to extend the depth of focus. The EDOF element 460 may produce a depth of focus for each meridian. Further, this depth of focus may indicate a sharp focus for each meridian at a broader range of foci. As used herein, sharp focus may be a focus that proves useful for vision, and that may be measured using a point spread function, defocus curves, a modulation transfer function (MTF), or by analysis of the Zernike polynomial, as will be understood to those skilled in the pertinent arts, for example.

As indicated by an MTF, for example, a retinal image may not suffer from astigmatism from any residual uncorrected power as a result of cornea and toric IOL mismatch or surgically induced astigmatism, if the uncorrected power is smaller than the depth of focus provided by the EDOF element of IOL 20. Similarly, the retinal image will not suffer from astigmatism when rotation of the IOL introduces an astigmatism that is smaller than the depth of focus provided by the EDOF element of IOL 20.

Various techniques for extending the depth of focus of an IOL have been proposed. For example, some approaches are based on a bulls-eye refractive principle, and involve a central zone with a slightly increased power. For these techniques, the EDOF element is typically independent of rotation due to a rotational symmetry of the EDOF element. In contrast, the present invention provides a single or limited number of diffractive EDOF structures that are rotationally asymmetric.

The present invention provides a lens that combines a base rotationally symmetric or asymmetric, toric, spherical or aspherical lens, with a rotationally asymmetric diffractive surface structure designed of a single or limited number of echelettes. This diffractive profile is such that it may be designed to extend the depth of focus of the postoperative eye. Further, the IOL of the present invention may preferably provide an extended depth of focus in all meridians. In some exemplary embodiments, the depth of focus is differential in that it is greater in some meridian(s) versus others. Fine tuning the differential extended depth of focus with the optic not only allows for achievement of the intended refractive outcome, but additionally makes the positioning of the IOL less critical in-situ.

Figure 3:
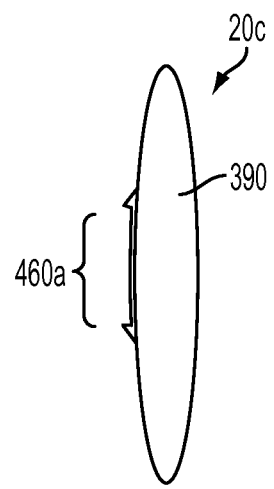
FIG. 3 is a schematic illustration of an ophthalmic lens according to embodiments of the present invention.
Figure 3A:
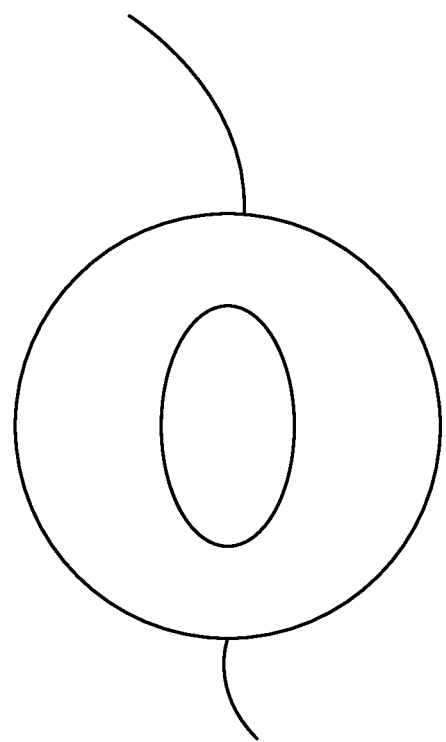
FIG. 3A is a top plan view of an ophthalmic lens according to embodiments of the present invention.
Figure 3B:
FIG. 3B is a side view of an ophthalmic lens according to embodiments of the present invention.
Figure 3C:
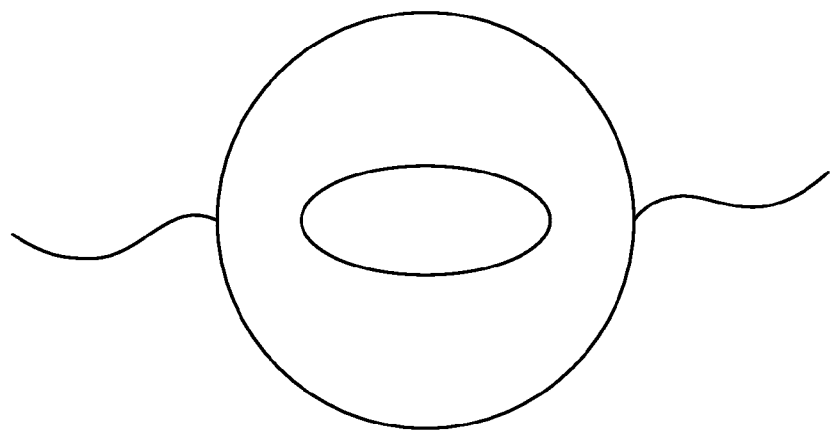
FIG. 3C is a top plan view of an ophthalmic lens according to embodiments of the present invention.
Figure 3D:
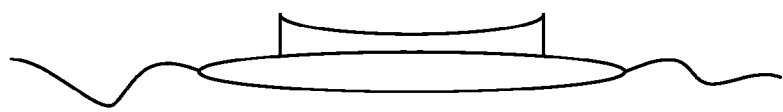
FIG. 3D is a side view of an ophthalmic lens according to embodiments of the present invention.

In a specific example illustrated in FIGS. 3-3D, the IOL of the present invention may be designed to correct astigmatism. A base refractive lens 390 for use with the present invention may be, for example, the Tecnis® lens offered by Abbott Medical Optics. A single rotationally asymmetric diffractive structure/echelette 460a upon the base refractive lens may be, in this particular example, elliptical in nature, and have a diffractive step height that varies along the ellipse. In this exemplary embodiment, the short axis of the ellipse may have a radius of about 0.663 millimeters, and a step height of $0.4232\lambda$ or 1.74 µm, and the long axis of the ellipse may have a radius of about 0.856 millimeters, and a step height of $0.5088\lambda$ or 2.05 µm. The stepheight may steadily and gradually change between the short axis from 1.74 µm to the long axis at 2.05 µm, or there may be an abrupt change from the stepheight of the short axis to the stepheight of the long axis at a location between the short and long axis.

Figure 3E:
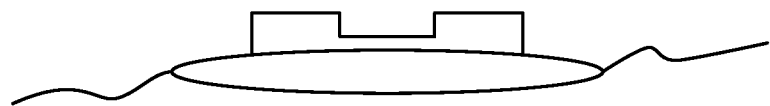
FIG. 3E is a side view of an ophthalmic lens according to embodiments of the present invention.
Figure 3F:
FIG. 3F is a side view of an ophthalmic lens according to embodiments of the present invention.

While the stepheights, as seen in FIGS. 3B and 3D smoothly and gradually transition from the lower stepheight at the short axis, to the higher stepheight at the long axis, other exemplary embodiments include abrupt transitions as seen in FIG. 3E, as well as other types of transitions, such as the sinusoidal transition seen in FIG. 3F.

Figure 4:
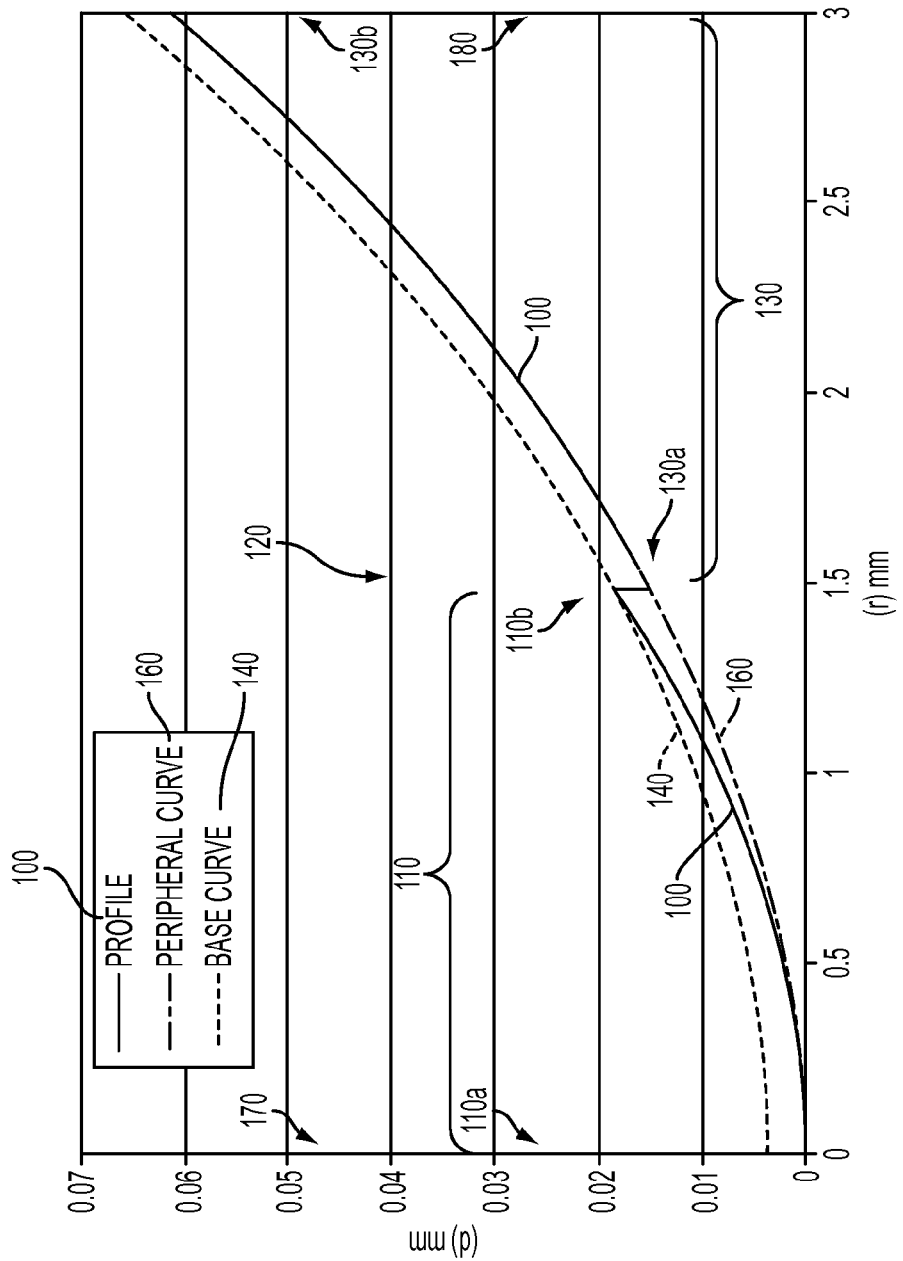
FIG. 4 shows aspects of a single microstructure lens according to embodiments of the present invention.

FIG. 4 discloses the general structure of single diffractive element. Only a cross section of half of the lens is shown in FIG. 4. Profile 100 of the single ring surface includes an inner portion or single ring 110, a step or transition 120, and an outer portion 130. Inner portion 110 extends between a central location 170 of profile 100 and transition 120, and outer portion 130 extends between transition 120 and a peripheral location 180 of profile 100. Central location 170 is typically disposed at the optical axis. Transition 120 is disposed at a distance of about 1.5 mm from the optical axis, and peripheral location 180 is disposed at the diameter of the clear aperture of the lens, here at a distance of about 3.0 mm from the optical axis. In some cases, transition 120 can be disposed at a distance from the optical axis that is within a range from about 0.5 mm to about 2.0 mm, and peripheral location 180 can be disposed at a distance from the optical axis that is within a range from about 2.0 to about 3.5 mm, or bigger (for example, for contact lenses, the ranges would be scaled due to the larger sizes of the contact lens compared to an IOL).

As shown in FIG. 4, the surface height or sag (d) from a reference plane perpendicular to the optical axis, of each point on the lens profile is plotted against the radial distance (r) from the optical axis of the lens. As shown here, the value of displacement or total sag (d) can have a value within a range from about 0 mm to about 0.07 mm. The total sag can depend on the refractive shape of the surface and can have a value, for an IOL, of typically between 0 mm and about 2 mm, or to about minus 2 mm, in cases where the surface is concave.

Inner Portion

Inner portion or echelette 110 includes a center 110a and a peripheral edge 110b. At center or central section 110a of inner portion 110, the sag (d) of inner portion 110 is substantially equivalent to the displacement or sag (d) of base curve plus offset 160. At peripheral edge 110b, the sag (d) of inner portion 110 is substantially equivalent to the sag (d) of base curve 140. Where radial distance (r) is zero, sag (d) of inner portion 110 is equivalent to the value of the base curve plus offset 160. The value of sag (d) between radial distance zero and radial distance at the peripheral edge 110b, for example at 1.5 mm, gradually and smoothly changes from the value of base curve plus offset 160 (at r=0) to base curve 140 (at r=1.5 mm) in a parabolic fashion. As shown here, inner portion 110 can present a parabolic shape, for example as described in Equation 4a of Cohen, Applied Optics, 31:19, pp. 3750-3754 (1992), incorporated herein by reference. In exemplary embodiments where the shape of the inner portion is asymmetric with respect to the optical axis, as for example in an ellipse, the peripheral edge 110b of the inner portion 110 may vary between about 0.5 mm and about 2.0 mm.

Transition

At the peripheral edge 110b, where the radial distance (r) is 1.5 mm, the value of sag (d) steps or changes from the value of base curve 140 to the value of base curve plus offset 160. Where radial distance (r) corresponds to transition 120, sag (d) of inner portion 110 is equivalent to the value of the base curve 140. Relatedly, the displacement of the profile 100 approaches that of the base curve plus offset 160 as the radial distance increases from a value of zero to a value of about 1.5 mm. The value of the offset can be determined along the vertical axis. The offset value may be selected depending on the amount of phase delay. According to one embodiment, the inner portion 110 and the outer portion 130 may not end up at the same vertical height at position 110b/130a. One way to connect these two endpoints is by using a straight vertical line. As shown here, the diffractive transition step provides a sharp step in the profile. In some cases the transition is characterized by a step height having a value within a range from about 0.5 microns and about 4 microns. As discussed above, in exemplary variable stepheight embodiments, the transition may be smooth and gradual from the low stepheight to the high stepheight, or may be abrupt.

Outer Portion

Outer portion 130 includes an inner or central edge 130a and a peripheral edge 130b. At inner edge 130a, the sag (d) of outer portion 130 is substantially equivalent to the sag (d) of base curve plus offset 160. At peripheral edge 130b, the sag (d) of outer portion 130 remains substantially equivalent to the sag (d) of base curve plus offset 160. The value of sag (d) for the outer portion 130 of profile 100 between radial distance 1.5 mm and radial distance 3.0 mm is equivalent to the value of base curve plus offset 160. The sag of the profile 100 and the base curve plus offset 160 are approximately equivalent between radial distance values of 1.5 mm and 3.0 mm.

The limited ring embodiments comprise of adding a limited number of echelettes to the above detailed single ring microstructure. In general such limited ring embodiments comprise of a limited number of echelettes that are either adjacent or non-adjacent to the inner central echelette and may or may not be separated by a refractive region.

Figure 4A:
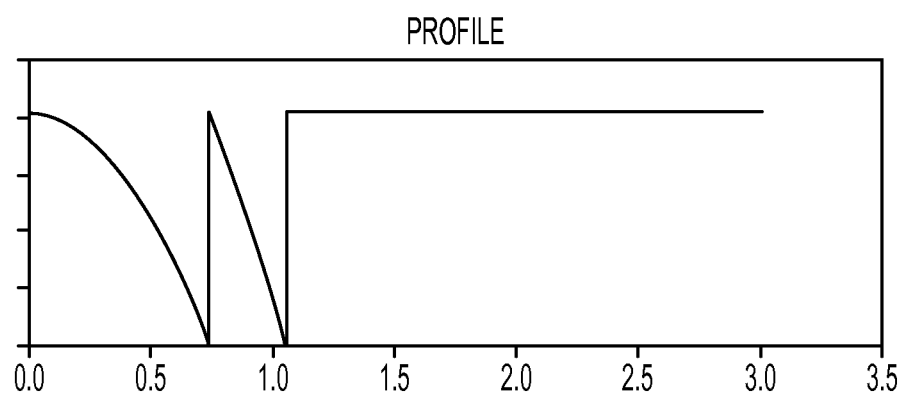
FIG. 4A shows aspects of a lens with a central and peripheral echelette according to embodiments of the present invention.

FIG. 4A provides a graphical representation of a portion of a lens diffractive profile with a central echelette and one peripheral adjacent echelette according to embodiments of the present invention. In FIG. 4A, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against p as shown in FIG. 4A. When plotted against radius r, optical zone 930 can have a shape or downward slope that is parabolic. Central and peripheral echelettes can have a surface area that is between 1 and 7 mm². For example, the echelettes may have a surface area that is 2.3 mm². An outer (refractive) zone can follow the base radius with a fixed offset. Exemplary embodiments include peripheral echelette(s) that are similar in shape (e.g. elliptical) and variable stepheight as the central echelette. Of course, this invention includes those embodiments where the peripheral echelette(s) differ in shape and/or variable stepheight as compared to the central echelette.

Although shown in the illustration as associated with the anterior surface of lens 390, those skilled in the art will appreciate that the asymmetric diffractive structure may alternatively be associated with the posterior surface of lens 390. Further, in preferred embodiments, the diffractive structure 460a may include a limited number of echelettes.

Figure 5:
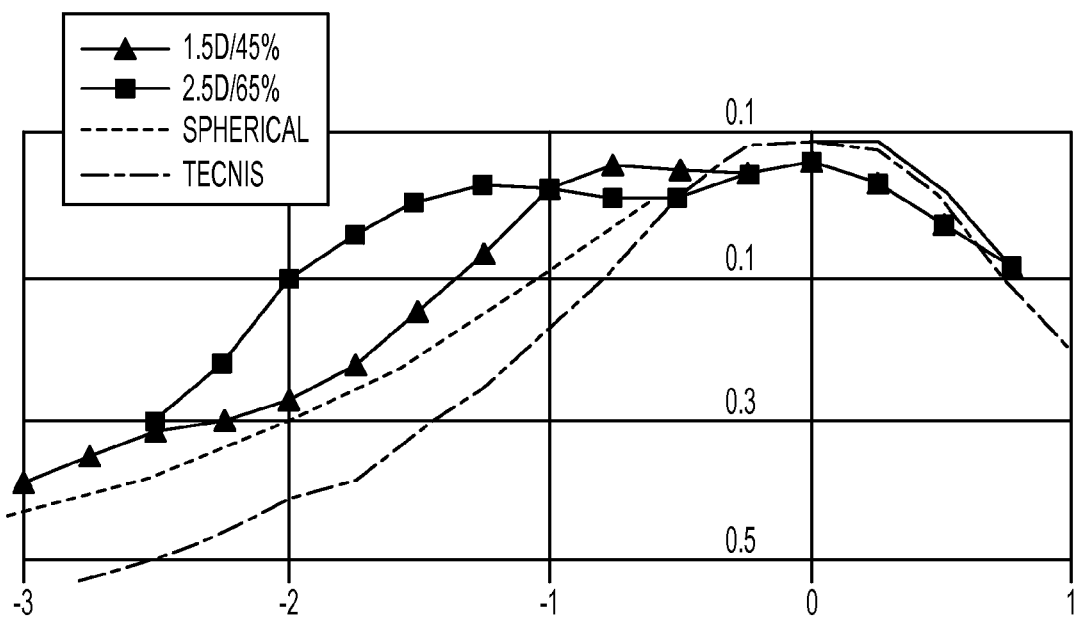
FIG. 5 is a graphical illustration of defocus curves.

FIG. 5 shows the predicted defocus curves, in accordance with axis parameters, for a Tecnis® lens, a spherical lens, and two lenses that are rotationally asymmetric with respect to both shape (ellipse) and stepheight. In the illustration of FIG. 5, the defocus curves are predicted for a 3 millimeter pupil, the horizontal access is the defocus in units of Diopters, and the vertical access is the visual acuity in units of logMAR. FIG. 5 discloses that the rotationally asymmetric lenses exhibit an extended depth of focus.

In an exemplary embodiment, the rotationally asymmetric design has an optical performance that depends on the pupil size. For very small pupils, where the pupil is smaller than the size of the ellipse, the echelette will act as a refractive lens, having a very large depth of focus, due to the pinhole effect. For higher and medium pupil sizes, where the pupil covers the central echelette and a part of the outer zone, the lens will act as a diffractive/refractive lens, with an appropriate phase shift. The size of the echelette influences the pupil dependence of the lens. As such, the size and shape of the echelette can be chosen, depending on the pupil sizes of a specific patient. For example, the pupil sizes of a patient may be measured in bright light, in dim light, during far vision and during near vision, and in the different combinations of light level and accommodative effort. These different pupil sizes, which may be defined as pupil dynamics, can be used as input parameters for an optimal design of the single ring or single echelette design. Additionally, with an elliptical shape, a differential depth of focus according to certain meridians may be utilized. That is, for a specific pupil size, certain parts of the pupil will be inside the wide region of the elliptically shaped echelette and thus the lens will act as a refractive lens, while other parts of the pupil will be outside of the elliptically shaped echelette, and thus the lens will acts as a diffractive with appropriate phase shift. Accordingly, based on these dynamics an appropriately shaped asymmetric structure may be designed to suit individual needs.

It should be appreciated that while the exemplary embodiment disclosed herein has rotationally asymmetry in both shape and stepheight, rotational asymmetry of either shape or stepheight alone may also result in extended depth of focus. In addition, although an elliptical structure is disclosed, it is envisioned that any number of rotationally asymmetric structures will result in an extended depth of focus.

The base refractive lens associated with the EDOF element of the present invention may be spherical or aspherical, and/or any type of toric design indicated to those skilled in the pertinent arts in light of the discussion herein. For example, the base refractive IOL may be toric, such as when larger amounts of corneal cylinder require correction. In such circumstances, the majority of the corneal cylinder may be corrected by the refractive toric IOL, and the diffractive element of the present invention may be added merely as a depth of focus element that makes the base toric IOL less sensitive to rotation and the choice of optical power. Additionally, the base refractive lens of the present invention may be combined with an accommodating IOL, and/or may further be used in combination with any type of ophthalmic lens.

The rotationally asymmetric diffractive EDOF element of the present invention may be combined with one or more other diffractive elements associated with the base refractive lens, such as the multifocal diffractive zones discussed hereinabove. Thereby, the sensitivity of the multifocal lens to residual corneal astigmatism may be reduced. As such, the present EDOF element may be used in conjunction with a bifocal lens or a trifocal lens. In some embodiments, corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present invention may be applied to inlays, onlays, accommodating IOLs, spectacles, and even laser vision correction.

Figure 6:
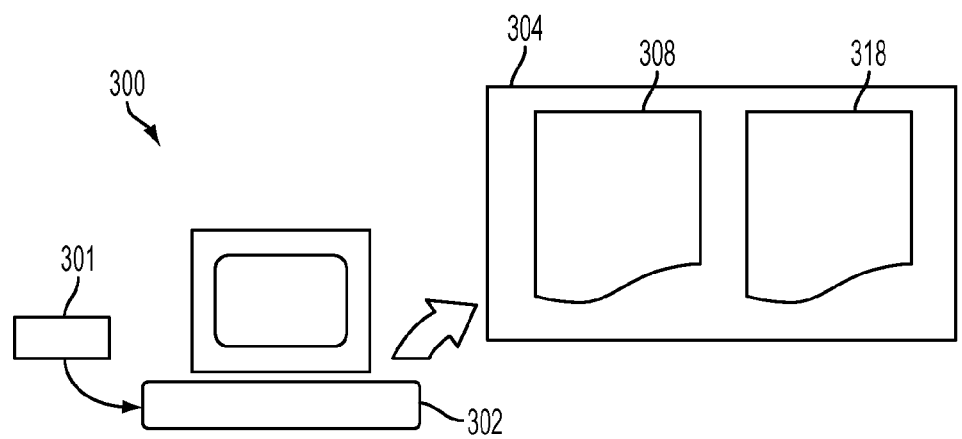
FIG. 6 is a block diagram illustrating a clinical computing system.

FIG. 6 is a block diagram illustrating the implementation of the present invention in a clinical system 300 comprised of one or more apparatuses that of capable of assessing the eye's biometry and of performing the calculations and comparisons set forth in designing the rotationally asymmetric diffractive EDOF element. The system 300 may include a biometric reader and/or input 301, a processor 302, and a computer readable memory 304 coupled to the processor 302. The computer readable memory 304 includes therein an array of ordered values 308 and sequences of instructions 318 which, when executed by the processor 302, cause the processor 302 to select and/or design the diffractive structures discussed herein for association with a lens to be implanted into the eye of the subject presenting the biometric readings at input 301. The array of ordered values 308 may comprise data used or obtained from and for use in design methods consistent with embodiments of the invention. For example, the array of ordered values 308 may comprise one or more desired refractive outcomes, parameters of an eye model based on one or more characteristics of at least one eye, and/or data related to an IOL, a set of IOLs, and one or more rotationally asymmetric echelettes.

The sequence of instructions 318 may include one or more steps consistent with embodiments of the invention. In some embodiments, the sequence of instructions 318 may include application of calculations, algorithms, customization, simulation, comparison, remote communications and networking, and the like.

The processor 302 may be embodied in a general purpose desktop or laptop computer, and/or may comprise hardware and/or software associated with inputs 301. In certain embodiments, the system 300 may be configured to be electronically coupled to another device, such as one or more instruments for obtaining measurements of an eye or a plurality of eyes. Alternatively, the system 300 may be embodied in a handheld device that may be adapted to be electronically and/or wirelessly coupled to one or more other devices.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereinafter.

What is claimed is:

1. An ophthalmic lens for correcting vision, comprising:
   an optic having at least a toric portion for correcting astigmatism and having a base cylinder power; and
   less than 4 rotationally asymmetric diffractive echelettes integrated with the lens for extending depth of focus, wherein the extended depth of focus reduces sensitivity of the optic to at least one of rotation and the base cylinder power.

2. The ophthalmic lens of claim 1, wherein the extended depth of focus differs between each meridian of the optic at a range of foci.

3. The ophthalmic lens of claim 1, wherein the echelettes are comprised of step heights that vary tangentially as a function of the rotational angle.

4. The ophthalmic lens of claim 1, wherein the echelettes are rotationally asymmetric with respect to the optical axis.

5. The ophthalmic lens of claim 1, wherein the toric portion comprises an anterior and/or posterior surface of said optic.

6. The ophthalmic lens of claim 1, wherein said toric portion comprises a radius of first curvature substantially aligned with a meridian of minimum optical power, and a second radius of curvature substantially aligned with a meridian of maximum optical power.

7. A vision corrective optic, comprising:
   a lens for correcting at least one aberration of an eye;
   a rotationally asymmetric depth of focus extender integrated with the lens, the depth of focus extender comprising less than four diffractive echelettes, wherein the depth of focus extender increases at least one of alignment tolerance and matching to the at least one aberration.

8. The vision corrective optic of claim 7, wherein said depth of focus extender is positioned on the anterior and/or posterior surface of the lens.

9. The vision corrective optic of claim 7, wherein said depth of focus extender is elliptical in shape.

10. The vision corrective optic of claim 7, wherein the depth of focus extender is rotationally asymmetric with respect to the optical axis.

11. The vision corrective optic of claim 7, wherein the depth of focus extender is comprised of echelettes with step heights that vary tangentially as a function of the rotational angle.

12. A method for making an ophthalmic lens that decreases sensitivity of astigmatic correction to errors of cylinder power selection and lens rotational alignment, comprised of integrating a rotationally asymmetric diffractive structure with less than 4 echelettes to a surface of an intraocular lens.

* * * * *